US011172910B2

United States Patent
Greenleaf et al.

(10) Patent No.: US 11,172,910 B2
(45) Date of Patent: Nov. 16, 2021

(54) ULTRASOUND VIBROMETRY WITH UNFOCUSED ULTRASOUND

(75) Inventors: James F. Greenleaf, Rochester, MN (US); Shigao Chen, Rochester, MN (US); Armando Manduca, Rochester, MN (US); Pengfei Song, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 726 days.

(21) Appl. No.: 14/001,604

(22) PCT Filed: Feb. 27, 2012

(86) PCT No.: PCT/US2012/026769
§ 371 (c)(1),
(2), (4) Date: Nov. 4, 2013

(87) PCT Pub. No.: WO2012/116364
PCT Pub. Date: Aug. 30, 2012

(65) Prior Publication Data
US 2014/0046173 A1    Feb. 13, 2014

Related U.S. Application Data

(60) Provisional application No. 61/446,839, filed on Feb. 25, 2011.

(51) Int. Cl.
*A61B 8/08*     (2006.01)
*G01N 29/07*    (2006.01)
(Continued)

(52) U.S. Cl.
CPC ............ *A61B 8/485* (2013.01); *A61B 5/0059* (2013.01); *A61B 8/5223* (2013.01); *G01N 21/17* (2013.01);
(Continued)

(58) Field of Classification Search
CPC ....... A61B 5/0059; A61B 8/461; A61B 8/485; A61B 8/5223; G01N 21/17;
(Continued)

(56) References Cited

U.S. PATENT DOCUMENTS 4,441,503 A    4/1984  O'Donnell
5,606,971 A    3/1997  Sarvazyan
(Continued)

FOREIGN PATENT DOCUMENTS

CN    101883526 A    11/2010

OTHER PUBLICATIONS

P Song, MW Urban, A Manduca, H Zhao, JF Greenleaf, S Chen. "Comb-push Ultrasound Shear Elastography (CUSE) with Various Ultrasound Push Beams." IEEE Trans Med Imag: 32(8): 1435-1447. Aug. 2013.*

(Continued)

*Primary Examiner* — Amanda Lauritzen Moher
(74) *Attorney, Agent, or Firm* — Quarles & Brady LLP

(57) ABSTRACT

Methods for measuring mechanical properties of an object or subject under examination with an ultrasound system and using unfocused ultrasound energy are provided. Shear waves that propagate in the object or subject are produced by applying unfocused ultrasound energy to the object or subject, and measurement data is acquired by applying focused or unfocused ultrasound energy to at least one location in the object or subject at which shear waves are present Mechanical properties are then calculated from the acquired measurement data.

10 Claims, 13 Drawing Sheets

(51) Int. Cl.
| | |
|---|---|
| G01N 21/17 | (2006.01) |
| G01N 29/24 | (2006.01) |
| G01N 29/22 | (2006.01) |
| G01S 7/52 | (2006.01) |
| A61B 5/00 | (2006.01) |
| G01R 33/48 | (2006.01) |
| G01S 15/89 | (2006.01) |
| A61B 8/00 | (2006.01) |

(52) U.S. Cl.
CPC ......... *G01N 29/075* (2013.01); *G01N 29/221* (2013.01); *G01N 29/2456* (2013.01); *G01R 33/4814* (2013.01); *G01S 7/52042* (2013.01); *A61B 8/461* (2013.01); *G01N 2291/02475* (2013.01); *G01N 2291/02827* (2013.01); *G01N 2291/0422* (2013.01); *G01S 15/8927* (2013.01)

(58) Field of Classification Search
CPC ......... G01N 2291/02475; G01N 2291/02827; G01N 2291/0422; G01N 29/075; G01N 29/221; G01N 29/2456; G01R 33/4814
See application file for complete search history.

(56) References Cited

U.S. PATENT DOCUMENTS

| | | | |
|---|---|---|---|
| 5,810,731 | A | 9/1998 | Sarvazyan et al. |
| 7,252,004 | B2* | 8/2007 | Fink et al. ............. 73/597 |
| 7,753,847 | B2 | 7/2010 | Greenleaf et al. |
| 7,785,259 | B2 | 8/2010 | Zheng et al. |
| 9,345,448 | B2* | 5/2016 | Fatemi ............ A61B 8/0858 |
| 10,863,968 | B2* | 12/2020 | Rosado-Mendez ................... G01S 15/8927 |
| 2004/0068184 | A1* | 4/2004 | Trahey ............ G01S 15/8927 600/438 |
| 2004/0210134 | A1* | 10/2004 | Hynynen et al. ............ 600/439 |
| 2005/0252295 | A1 | 11/2005 | Fink et al. |
| 2007/0038095 | A1* | 2/2007 | Greenleaf et al. ............ 600/438 |
| 2009/0178483 | A1* | 7/2009 | Angelsen ................ A61B 8/08 73/597 |
| 2009/0216119 | A1 | 8/2009 | Fan et al. |
| 2010/0036244 | A1* | 2/2010 | Angelsen ................ A61B 8/08 600/438 |
| 2010/0168566 | A1* | 7/2010 | Bercoff ................ A61B 8/08 600/438 |
| 2010/0312116 | A1* | 12/2010 | Pernot ................ A61B 8/0883 600/453 |
| 2011/0066030 | A1* | 3/2011 | Yao ................ A61B 8/0833 600/438 |
| 2011/0184287 | A1* | 7/2011 | McAleavey ............ 600/438 |
| 2011/0245678 | A1* | 10/2011 | Tamura ................ A61B 8/08 600/453 |
| 2011/0263978 | A1* | 10/2011 | Chen ................ A61B 8/48 600/438 |
| 2012/0089019 | A1* | 4/2012 | Fan ................ A61B 8/485 600/437 |
| 2012/0095323 | A1* | 4/2012 | Eskandari ............ A61B 5/0051 600/411 |
| 2012/0116220 | A1* | 5/2012 | Burcher ................ A61B 5/0048 600/438 |
| 2012/0123262 | A1* | 5/2012 | Xie ................ A61B 5/0048 600/438 |
| 2013/0218012 | A1* | 8/2013 | Specht ................ G01S 15/8979 600/438 |
| 2014/0018679 | A1* | 1/2014 | Chen et al. ............ 600/438 |
| 2014/0296709 | A1* | 10/2014 | Fatemi et al. ............ 600/438 |
| 2018/0317887 | A1* | 11/2018 | Greenleaf ............ G01S 15/8927 |

OTHER PUBLICATIONS

P Song, H Zhao, A Manduca, MW Urban, JF Greenleaf, S Chen. "Comb-push Ultrasound Shear Elastography (CUSE): A Novel Method for Two-Dimensional Shear Elasticity Imaging of Soft Tissues." IEEE Trans Med Imag: 31(9): 1821-1832. Sep. 2012.*

H Zhao, P Song, MW Urban, JF Greenleaf, S Chen. Robust Shear Wave Speed Measurement Using Comb-push Ultrasound Radiation Force. Ultrasonics Symposium (IUS), 2011 IEEE International, 1270-1273.*

S Chen, MW Urban, C Pislaru, R Kinnick, Y Zheng, A Yao, JF Greenleaf. "Shearwave Dispersion Ultrasound Vibrometry (SDUV) for Measuring Tissue Elasticity and Viscosity." IEEE Trans Ultrason Ferroelectr Freq Cntrl: 56(1): 55-62. Jan. 2009.*

H Zhao, P Song, MW Urban, JF Greenleaf, S Chen. "Shear Wave Speed Measurement Using an Unfocused Ultrasound Beam." Ultrasound in Medicine and Biology: 38(9): 1646-1655. May 2012.*

PA Meyer et al. "Ultrasonic Testing Using Phased Arrays." ROMA 2000 15th WCNDT. Lewiston, PA USA.*

Chen, Shigao; Zhao, Heng; Song, Pengfei; Urban, Matthew W.; Greenleaf, James F. 2011 IEEE International Ultrasonics Symposium, Jan. 1, 2011, p. 1171-1174, 4p. Publisher: IEEE.*

Deffieux et al. "On the Effects of Reflected Waves in Transient Shear Wave Elastography." IEEE Transactions on Ultrasonics, Ferroelectrics, and Frequency Control, vol. 58, No. 10, Oct. 2011, pp. 2032-2035.*

Manduca et al. "Spatio-temporal directional filtering for improved inversion of MR elastography images." Medical Image Analysis 7, 2003, pp. 465-473.*

Song et al. "Fast shear compounding using directional filtering and two-dimensional shear wave speed calculation," 2013 IEEE International Ultrasonics Symposium (IUS), 2013, pp. 1264-1267.*

International Search Report and Written Opinion under dated Jul. 17, 2012 in connection with PCT/US2012/026769.

The State Intellectual Property Office of the People's Republic of China, Search Report and First Office Action, Application No. 201280020131.5, dated Nov. 24, 2014, 18 pages.

Extended European Search Report dated Dec. 12, 2017 from related EP Application No. 12749825.1, 7 pages.

* cited by examiner

ULTRASOUND VIBROMETRY WITH UNFOCUSED ULTRASOUND

CROSS-REFERENCE TO RELATED APPLICATIONS

This application represents the national stage entry of PCT International Application No. PCT/US2012/026769 filed on Feb. 27, 2012 and claims the benefit of U.S. Provisional Patent Application Ser. No. 61/446,839 filed Feb. 25, 2011. The contents of both of these applications are hereby incorporated by reference as if set forth in their entirety herein.

STATEMENT REGARDING FEDERALLY SPONSORED RESEARCH

This invention was made with government support under DK082408 and EB132640 awarded by the National Institutes of Health. The government has certain rights in the invention.

BACKGROUND OF THE INVENTION

The field of the invention is systems and methods for ultrasound. More particularly, the invention relates to systems and methods for ultrasound vibrometry, in which ultrasound is used to measure mechanical properties of a material or tissue of interest.

Characterization of tissue mechanical properties, particularly the elasticity or tactile hardness of tissue, has important medical applications because these properties are closely linked to tissue state with respect to pathology. For example, breast cancers are often first detected by the palpation of lesions with abnormal hardness. In another example, a measurement of liver stiffness can be used as a non-invasive alternative for liver fibrosis staging.

Recently, an ultrasound technique for measuring mechanical properties of tissues, such as elasticity and viscosity, called shear-wave dispersion ultrasound vibrometry ("SDUV") was developed. This SDUV technique is described, for example, in co-pending U.S. Pat. Nos. 7,785,259 and 7,753,847, which are herein incorporated by reference in their entirety. In these and similar methods, a focused ultrasound beam, operating within FDA safety limits, is applied to a subject to generate harmonic shear waves in a tissue of interest. The propagation speed of the induced shear wave is frequency dependent, or "dispersive," and relates to the mechanical properties of the tissue of interest. Shear wave speeds at a number of frequencies are measured by pulse echo ultrasound and subsequently fit with a theoretical dispersion model to inversely solve for tissue elasticity and viscosity. These shear wave speeds are estimated from the phase of tissue vibration that is detected between two or more points with known distance along the shear wave propagation path.

Examples of other methods for calculating the mechanical properties of an object under examination using ultrasound energy are U.S. Pat. Nos. 5,606,971 and 5,810,731. However, like the aforementioned SDUV techniques, the methods presented in these patents require the use of focused ultrasound to produce vibratory motion in the object or subject under examination.

It would be desirable to provide a method for calculating mechanical properties of an object or subject under examination using ultrasound energy without the high level of ultrasound intensities currently required with focused ultrasound, while maintaining adequate levels of signal-to-noise ratio.

SUMMARY OF THE INVENTION

The present invention overcomes the aforementioned drawbacks by providing a method for measuring a mechanical property of a subject with an ultrasound system using unfocused ultrasound energy.

It is an aspect of the invention to provide a method for measuring a mechanical property of a subject with an ultrasound system. The method includes producing shear waves that propagate in the subject by applying unfocused ultrasound energy to the subject and acquiring measurement data by using a detection device to measure at least one location in the subject in which the produced shear waves are present. A mechanical property of the subject is then calculated using the acquired measurement data.

It is another aspect of the invention that measurement data may be acquired using an ultrasound device to apply ultrasound energy to the at least one location in the subject, or using at least one of an optical detection device, a magnetic resonance imaging device, and a microwave detection device to apply electromagnetic energy to the at least one location in the subject.

It is yet another aspect of the invention that the unfocused ultrasound energy applied to the subject includes a plurality of unfocused ultrasound beams extending outward from an ultrasound transducer in a comb-shaped pattern. These unfocused ultrasound beams may be spaced evenly or unevenly across the surface of the ultrasound transducer.

It is yet another aspect of the invention that a directional filter be applied to the measurement data acquired when using unfocused ultrasound energy produced in a comb-shaped pattern so that measurements that result in destructive interference are substantially mitigated.

It is yet another aspect of the invention that a first subset of measurement data corresponding to measurements of left-to-right shear waves be formed from the acquired measurement data, and that a second subset of measurement data corresponding to measurements of right-to-left shear waves be formed from the acquired measurement data. The first and second subsets are then selectively combined.

It is yet another aspect of the invention that unfocused ultrasound energy be applied to a planar region in the subject by energizing a plurality of ultrasound transducer elements along a first direction of an ultrasound transducer, such that the shear waves propagate along a direction extending outward from the planar region. An ultrasound device may then be used to acquire measurement data by applying ultrasound energy to the at least one location in the subject by energizing a plurality of ultrasound transducer elements along a second direction of an ultrasound transducer that is perpendicular to the first direction.

It is an aspect of the invention to provide a method for measuring a mechanical property of a subject with an ultrasound system. The method includes applying unfocused ultrasound energy to a subject in order to produce a plurality of tissue deformations therein at a plurality of axial depths. Measurement data is then acquired from the subject by applying ultrasound energy to at least one location in the subject at which at least one of the plurality of tissue deformations is located. A mechanical property of the subject is calculated using this acquired measurement data.

It is another aspect of the invention that the ultrasound energy applied to acquire measurement data is at least one of focused ultrasound energy and unfocused ultrasound energy.

It is yet another aspect of the invention that the unfocused ultrasound energy is applied to the subject to produce a plurality of shear waves propagating therein.

It is an aspect of the invention to provide a method for measuring a mechanical property of a subject with an ultrasound system that includes an ultrasound transducer. The ultrasound transducer is used to produce shear waves that propagate in the subject in at least one direction extending outward from the ultrasound transducer by applying ultrasound energy to the subject such that the ultrasound energy produces a force in the direction substantially normal to the surface of the ultrasound transducer. Measurement data is acquired by applying ultrasound energy to at least one location in the subject in which the shear waves are present. A mechanical property of the subject is then calculated using the acquired measurement data.

It is another aspect of the invention that the produced shear waves propagate in a direction substantially normal to a surface of the ultrasound transducer.

It is yet another aspect of the invention that at least one of the produced shear waves is a spherical wave that propagates radially outward from a point on a surface of the ultrasound transducer.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Mechanical properties of tissue such as elasticity and viscosity are useful parameters to differentiate healthy tissues from abnormal tissues. Thus, measurements of these properties have important medical applications. These mechanical properties are related to shear wave speed within the studied medium; therefore, shear waves generated by ultrasound within a tissue can be detected and used to estimate the mechanical properties of the studied tissue. It is an aspect of the present invention that unfocused ultrasound waves may be implemented to produce shear waves suitable for the interrogation of mechanical properties in an object or subject under examination. By way of example, unfocused ultrasound waves include ultrasound waves that are not electronically focused. In such instances, some weak focusing of the ultrasound waves may occur due to the acoustic lens of the ultrasound transducer.

Figure 1:
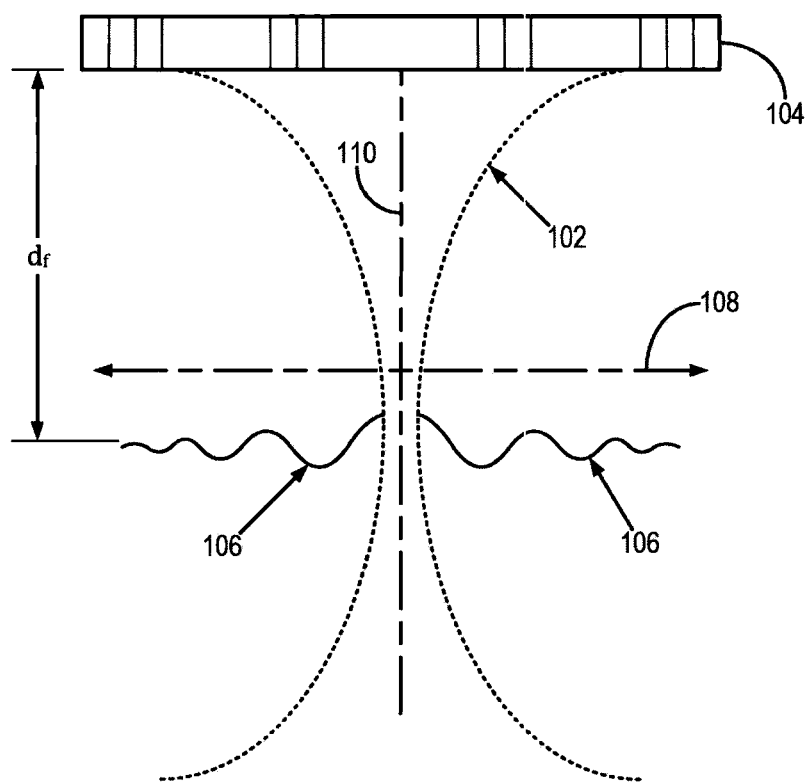
FIG. 1 is a pictorial representation of an example of a focused ultrasound beam that produces shear waves propagating outward from the focused ultrasound beam at a focus depth.

Referring to FIG. 1, an example of a previous focused ultrasound configuration is illustrated. In this configuration, a focused ultrasound beam 102 is produced by an ultrasound transducer 104. Resulting from the application of this focused ultrasound beam, shear waves 106 are generated. These shear waves propagate along a propagation direction 108 that extends outward from a push axis 110.

Figure 2A:
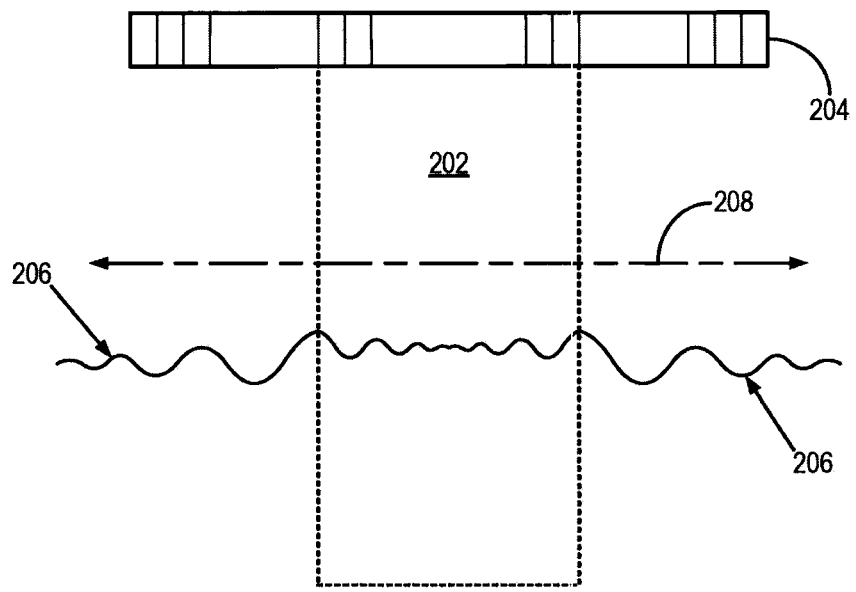
FIG. 2A is a pictorial representation of an example of an unfocused ultrasound beam that produces shear waves propagating outward from and inward into a region of insonification produced in response to the unfocused ultrasound.

Referring particularly to FIG. 2A, an example of a region of insonification 202 produced by unfocused ultrasound energy, such, as a tone burst, generated by an ultrasound transducer 204 is illustrated. The region of insonification 202 has a thickness that depends on the in-plane size of the transducer elements and a width that depends on the total width of the transducer elements used for insonification. This ultrasound energy produces a radiation force throughout the region of insonification 202. This radiation force causes region of insonification 202 to move towards or away from the transducer 204. At the edges of the region of insonification 202 shear waves 206 are produced and propagate along a propagation axis 208 that is normal to the edge of the region of insonification 202. Thus, the shear waves 206 propagate in two directions, outward from the region of insonification 202 and inward toward the center of region of insonification 202. Some shear waves 206 propagate in the out-of-plane direction with respect to the ultrasound transducer 204 and, therefore, cannot be imaged by a one-dimensional transducer, such as the one shown in FIG. 2A. However, such shear waves 206 can be imaged using a higher-dimensional transducer, such as a two-dimensional transducer.

Figure 2B:
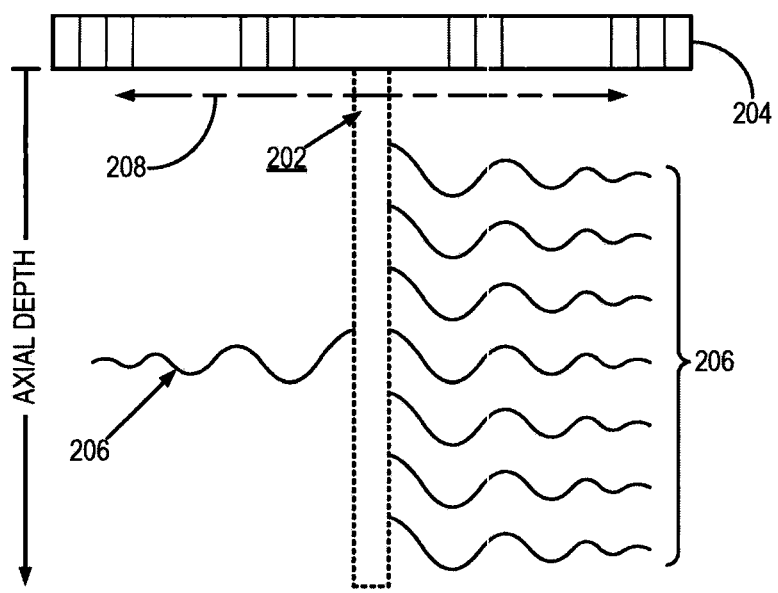
FIG. 2B is a pictorial representation of another example of an unfocused ultrasound beam that produces shear waves propagating at a plurality of axial depth outward from a region of insonification produced in response to the unfocused ultrasound.

As illustrated in FIG. 2B, shear waves 206 are produced along the full extent of the region of insonification 202. Thus, by using unfocused ultrasound to produce multiple shear waves 206, multiple parameters may be varied to make imaging consistent with the desired task. In this manner, a wide range of parameters can be varied in order to tailor the imaging at hand. As also illustrated in FIG. 2B, if the unfocused ultrasound beam is narrow, out-of-plane shear waves will no longer be plane waves; rather, the shear waves will be similar to a cylindrical wave emanating from the narrow ultrasound beam. In previous focused ultrasound methods, such as the scenario illustrated in FIG. 1, when a focused ultrasound beam is used, shear wave measurements were limited to the ultrasound axial depth corresponding to the focus depth, $d_f$. However, with the present method, shear waves generated by unfocused ultrasound are relatively uniform along the ultrasound axial depth. Therefore, measurements can be made at all axial depths, and not just one prescribed depth, such as the focus depth in focused ultrasound techniques.

Figure 2C:
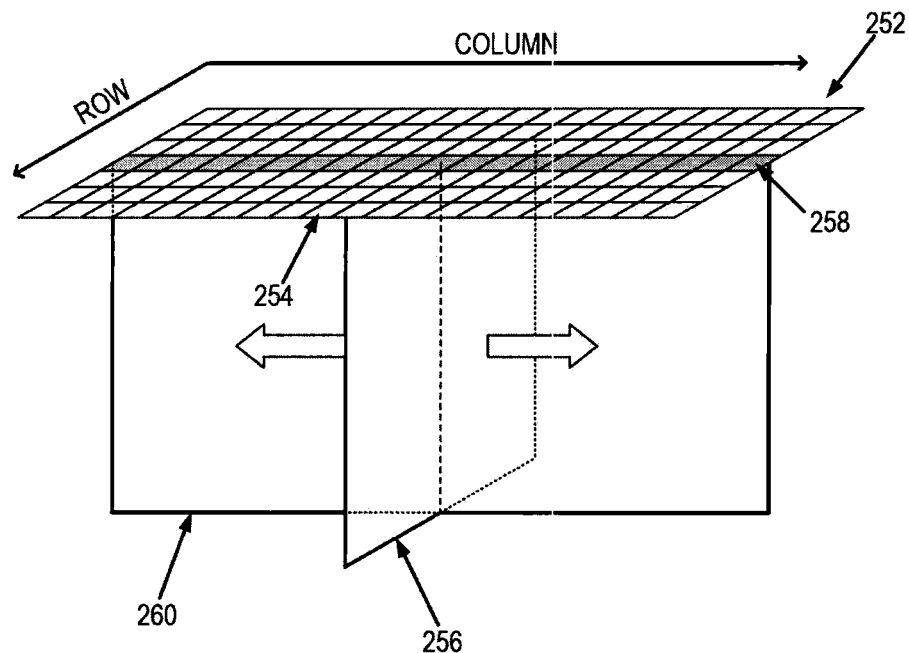
FIG. 2C is a pictorial representation of a two-dimensional array ultrasound transducer for imaging out-of-plane shear waves.

Referring now to FIG. 2C, another example of how unfocused ultrasound may be used to generate propagating shear waves or other tissue deformation is illustrated. In this example, multiple collinear elements in a two-dimensional ultrasound transducer array 252 are energized to produced a planar ultrasound beam that is unfocused along an axis of the ultrasound transducer. By way of example, one or more columns of transducer elements 254 may be energized to produce a planar ultrasound beam 256 that is unfocused along the column direction of the transducer 252. If desired, a small delay may be introduced across the columns 254 to simulate the acoustic lens on a one-dimensional transducer. These small delays will result in elevational focusing. The push transmission illustrated in FIG. 2C will produce out-of-plane shear waves that propagate out of the push plane (i.e., the plane defined by the planar ultrasound beam 256), as indicated by the white arrows. One or more rows of transducer elements 258 may then be used to image the propagation of the shear waves. By way of example, one or more rows may be energized to produce detection pulses in a plane 260.

Referring again to FIG. 1, the shear waves produced by a focused ultrasound beam will be similar to a cylindrical wave emanating from the narrow ultrasound beam 102. Therefore, the amplitude of the shear wave decreases rapidly as it propagates outwards from the push axis 110 because the shear wave energy is distributed over a larger area as the wave propagates outwards from the push axis 110. This effect can be called "geometric attenuation." In contrast, the out-of-plane shear wave produced in FIG. 2C is close to a planar shear wave and, therefore, is not subject to geometric attenuation. As a result, the out-of-plane shear wave, such as the one illustrated in FIG. 2C, can propagate over longer distances, which is highly advantageous because shear waves produced by ultrasound are usually very weak and can only propagate over a very short distance.

Figure 2D:
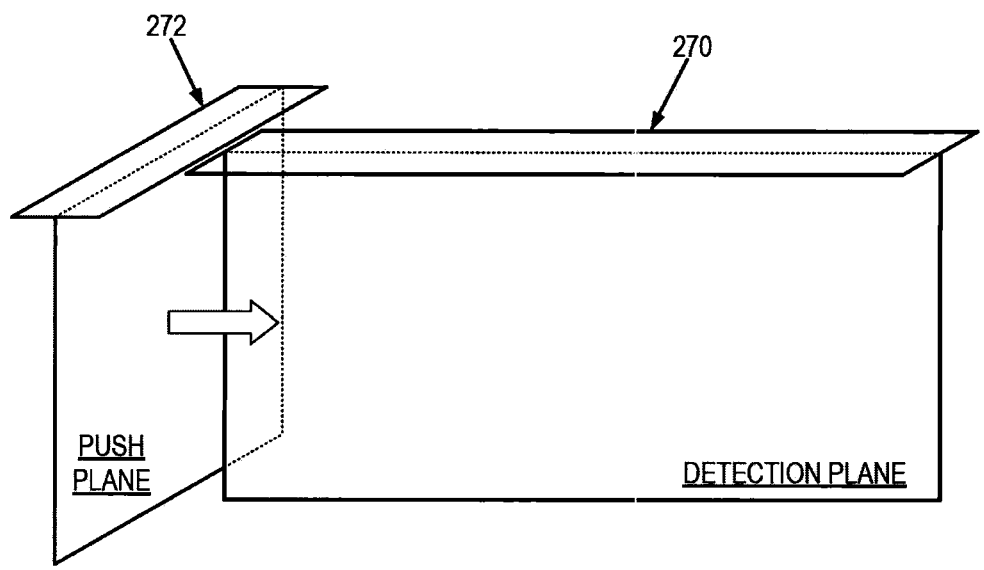
FIG. 2D is a pictorial representation of two ultrasound transducers used for imaging out-of-plane shear waves.

For a one-dimensional transducer array 270, a small push transducer 272 can be attached to one side of the transducer array 270, as illustrated in FIG. 2D. The out-of-plane shear wave can then be detected by the one-dimensional array transducer 270. As an example, the push transducer 272 may be a single element transducer with a fixed elevational focus. The push transducer 272 can be clipped to the one-dimensional array transducer 270 and fired by a single signal source through an external amplifier. An example of a signal source is the signal from a continuous-wave Doppler probe port of an ultrasound scanner. In another configuration, a second push transducer can be attached to the other side of the one-dimensional array transducer 270 to produce out-of-plane shear waves from both sides.

Figure 3A:
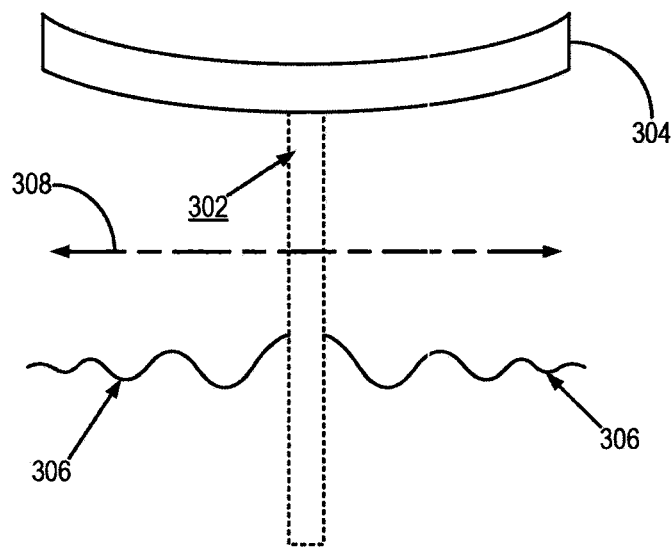
FIG. 3A is a pictorial representation of an example of an unfocused ultrasound beam generated by a curvilinear transducer array that produces shear waves propagating outward from a region of insonification produced in response to the unfocused ultrasound.
Figure 3B:
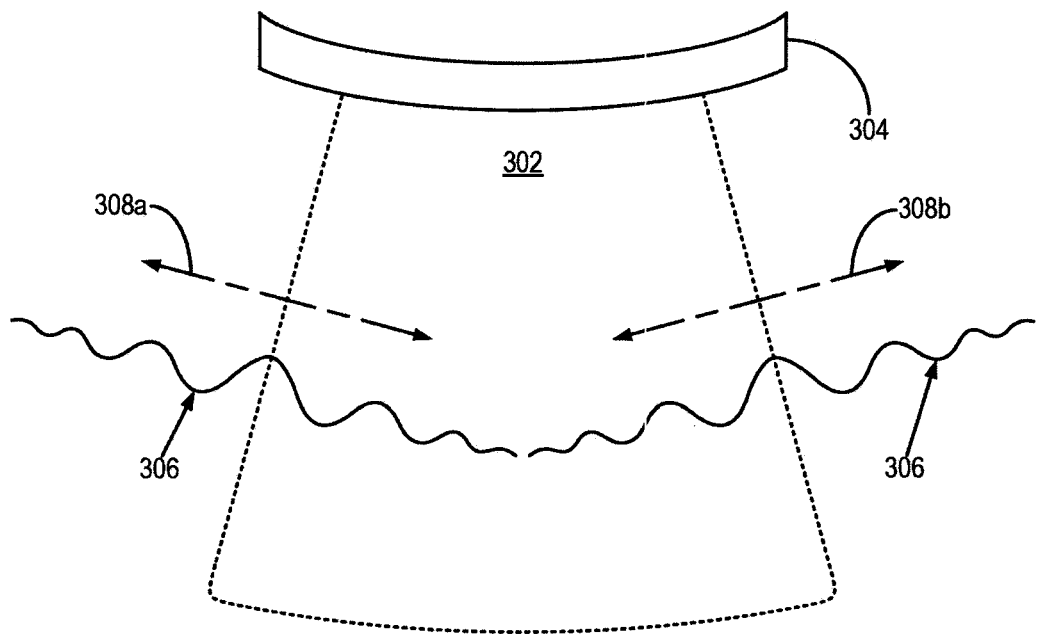
FIG. 3B is a pictorial representation of an example of an unfocused ultrasound beam generated by a curvilinear transducer array that produces shear waves propagating outward from and inward into a region of insonification produced in response to the unfocused ultrasound.

Referring now to FIGS. 3A and 3B, a region of insonification 302 can also be produced by unfocused ultrasound energy generated by a curvilinear array transducer 304. A narrow unfocused beam and a wide unfocused beam can generate different shear wave propagation patterns as shown in FIGS. 3A and 3B. For the wide unfocused beam illustrated in FIG. 3B, the center of the region of insonification 302 under the curvilinear array transducer 304 will see two shear waves crossing each other at an angle. This effect can be used for angle compound imaging.

Figure 4A:
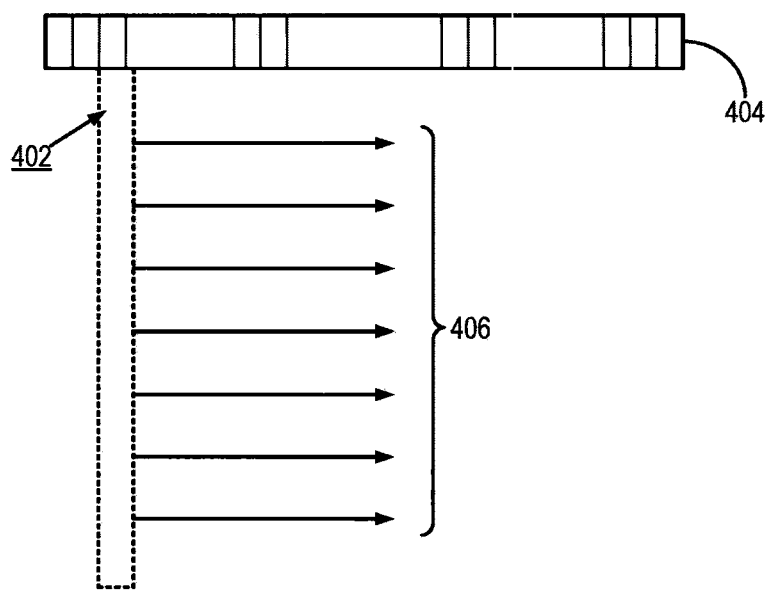
FIG. 4A is a pictorial representation of an example of an unfocused ultrasound beam generated off-center of an ultrasound transducer to produce shear waves propagating outward from a region of insonification produced in response to the unfocused ultrasound.
Figure 4B:
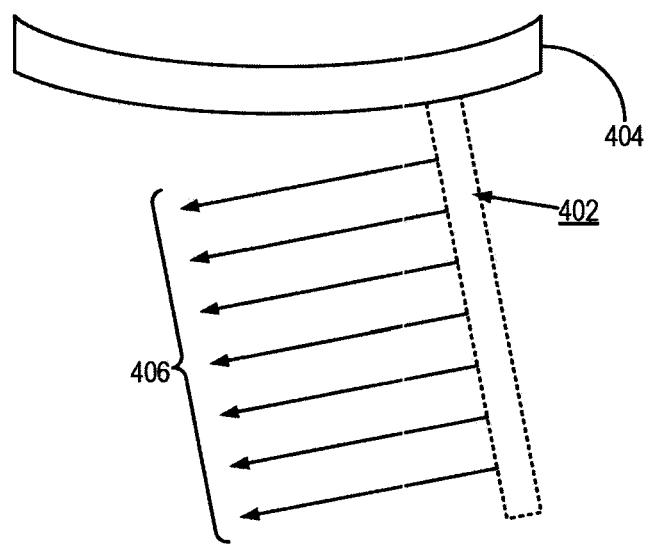
FIG. 4B is a pictorial representation of an example of an unfocused ultrasound beam generated off-center of a curvilinear ultrasound transducer to produce shear waves propagating outward from a region of in sonification produced in response to the unfocused ultrasound.

The unfocused beam does not need to be produced from the center of the transducer as shown in FIGS. 2A-3B above. Rather, the unfocused ultrasound energy 402 can be transmitted off-center from the transducer 404, thereby generating shear waves 406, as shown in FIGS. 4A and 4B.

Figure 5:
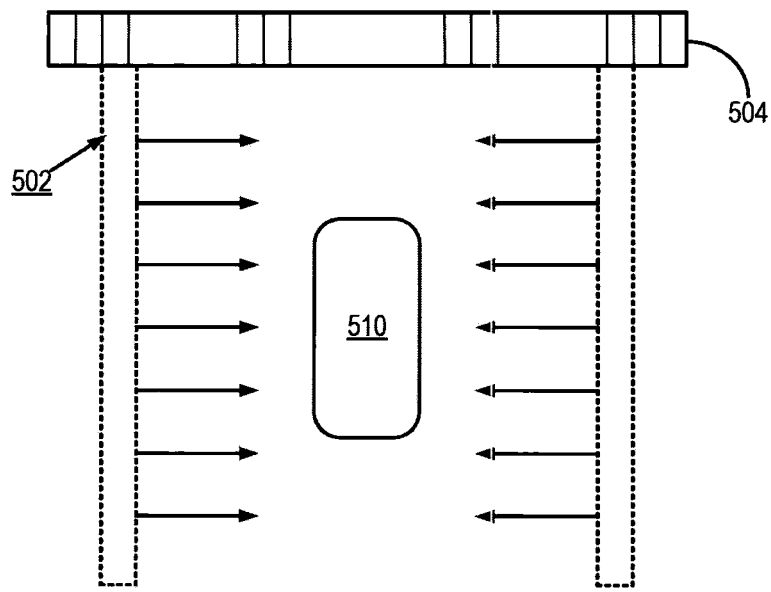
FIG. 5 is a pictorial representation of an example of two unfocused ultrasound beams generated off-center of an ultrasound transducer to produce shear waves propagating outward from respective regions of insonification produced in response to the unfocused ultrasound, such that the shear waves interact within an object or subject disposed between said unfocused ultrasound beams.

Referring to FIG. 5, in the case of a region-of-interest ("ROI") 510 containing, for example, a lesion, unfocused ultrasound energy can be produced as a single beam, or as a pair of beams, that is transmitted to either side, or both sides, of the ROI 510. The generated shear waves will propagate across the ROI 510, thereby facilitating estimations of the shear wave speed in the ROI 510.

Figure 6:
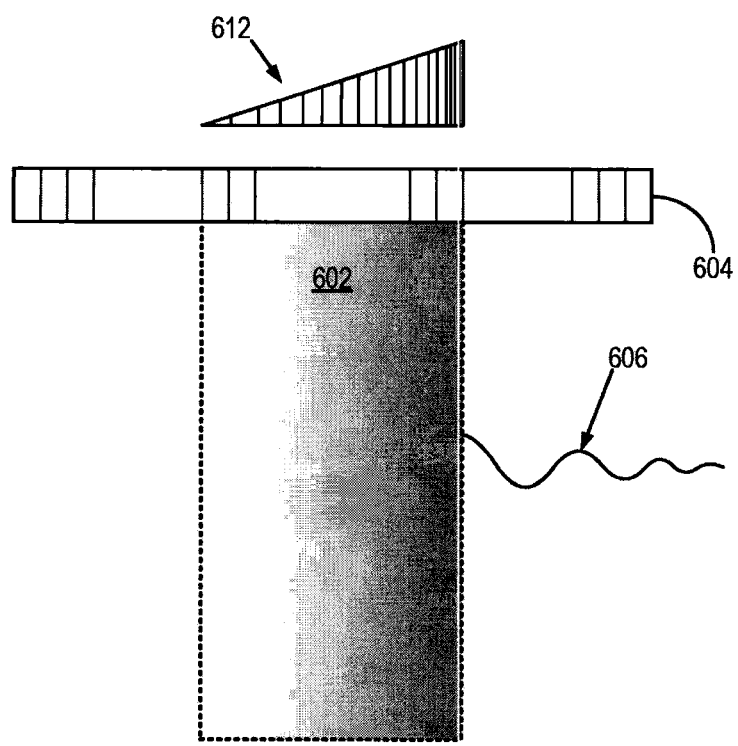
FIG. 6 is a pictorial representation of an example of an apodized, unfocused ultrasound beam generated that produces shear waves propagating outward from a region of insonification produced in response to the unfocused ultrasound.

Referring to FIG. 6, the transmission amplitude of the transducer elements can be weighted, for example, using a process referred to as apodization, to achieve desirable attributes of the generated shear waves. For example, apodization in the shape of a ramp 612 will produce a large shear gradient to the right of the region of insonification 602. Therefore, shear waves produced at the right edge of the region of insonification 602 will have different features as compared to shear waves produced at the left edge of the region of insonification 602. This difference in the characteristics of the shear waves may be beneficial for certain applications.

Figure 7:
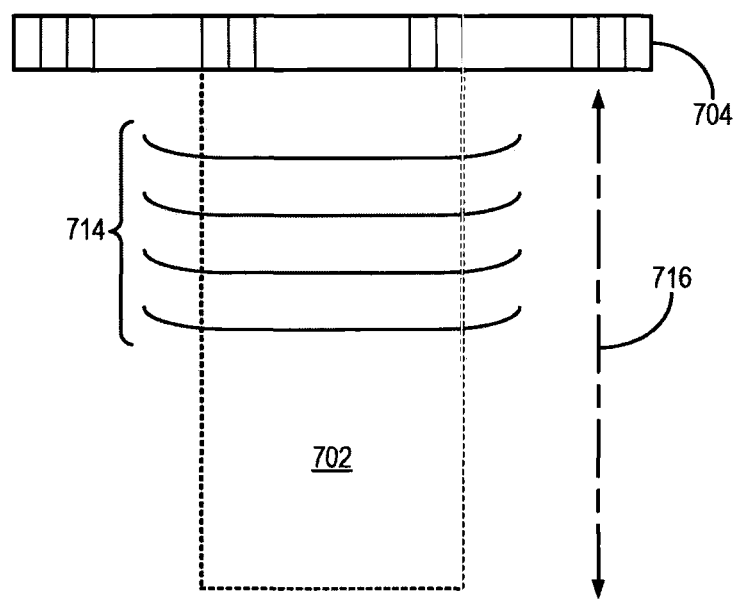
FIG. 7 is a pictorial representation of an example of an unfocused ultrasound beam used to produce shear waves propagating away from an ultrasound transducer in response to the unfocused ultrasound.

Referring now to FIG. 7, when the transducer 704 transmits a unfocused ultrasound beam, a force is produced on the material under investigation in the region of insonification 702 beneath the active elements of the transducer 704. This force can be caused by the radiation force of ultrasound, reflection of tissue motion at the tissue-transducer interface, or by mechanical displacement of the transducer elements in response to ultrasound energy. This downward force will produce a shear wave 714 propagating away from the transducer 704 along a propagation axis 716. In some instances, the wave front of this shear wave 714 can be circular, as if the shear wave 714 is emanating from a point at the surface of the transducer 704. Polarization of the shear wave 714 is in the direction extending away from the transducer 704 along the propagation axis 716 and, therefore, the shear wave 714 can be detected by the same ultrasound transducer 704. This effect can be used to interrogate the tissue in a longitudinal direction extending away from the transducer 704 rather than the lateral direction illustrated in FIGS. 1-6. This technique can be additionally useful for angle compounding. It is noted that the so-called "Fibroscan" studies shear waves in this longitudinal angle; however, there is an important distinction between the Fibroscan method and the method presented herein. In Fibroscan, shear waves are generated by mechanically vibrating a transducer with an external shaker, whereas the present method generates shear waves by transmitting ultrasound energy, such as tone bursts of unfocused ultrasound energy, without the need for a specialized mechanical vibrator. It should be appreciated by those skilled in the art that focused ultrasound may also be used to produce shear waves that propagate away from the transducer, similar to the aforementioned technique.

Figure 8:
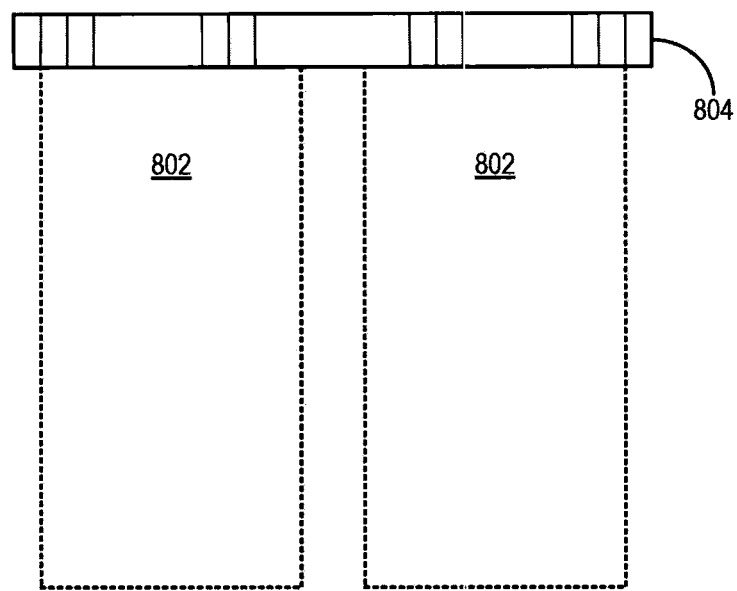
FIG. 8 is a pictorial representation of an example of two unfocused ultrasound beams produced in accordance with some embodiments of the present invention.

Other configurations of unfocused ultrasound energy can also be used to achieve the desired result. For example, and referring now to FIG. 8, two unfocused ultrasound energy beams may be produced in close proximity to each other, such that unique patterns of shear waves are generated in a region between those unfocused ultrasound beams.

Figure 9:
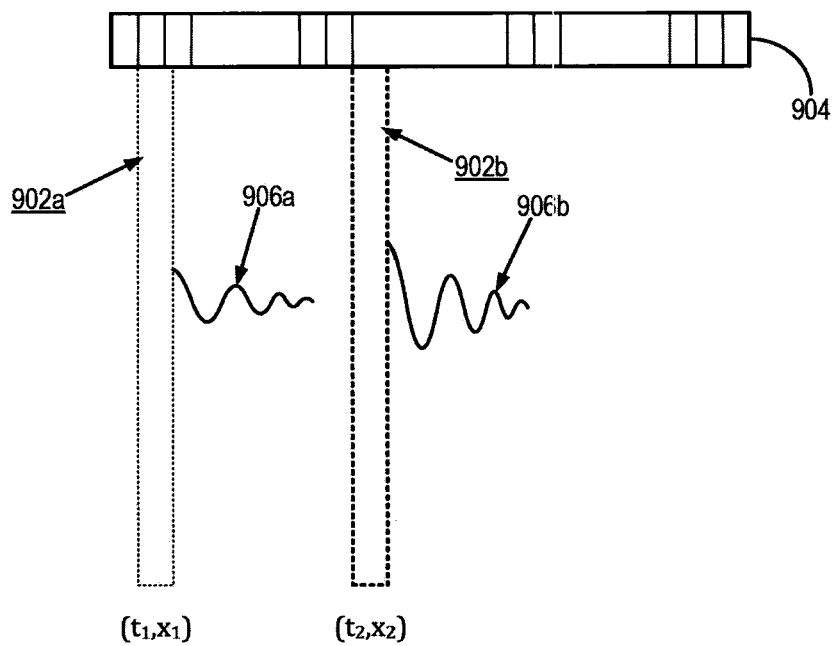
FIG. 9 is a pictorial representation of an example of multiple unfocused ultrasound beams being used to chase and amplify a propagating shear wave in accordance with some embodiments of the present invention.

Additionally, more than one tone burst of unfocused ultrasound energy can be used to follow the propagation of a shear wave as it travels through different locations. For example, and referring now to FIG. 9, an ultrasound beam can be transmitted to produce a first region of insonification 902a at a time, $t_1$, and a location, $x_1$, to generate a shear wave 906a. Then, another ultrasound beam can be transmitted to produce a second region of insonification 902b at a time, $t_2$, and a location, $x_2$. The location, $x_2$, is selected to be the location at which the shear wave 906a arrives at the time, $t_2$. The results of the application of the second ultrasound energy is the production of a shear wave 906b that has a higher amplitude than shear wave 906a.

It will be appreciated by those skilled in the art that the previously described concepts and techniques can be readily combined for different applications. For example, the two ultrasound beams in FIG. 8 can have apodization as shown in FIG. 6, and can also be used to chase or enhance a shear wave.

Figure 10A:
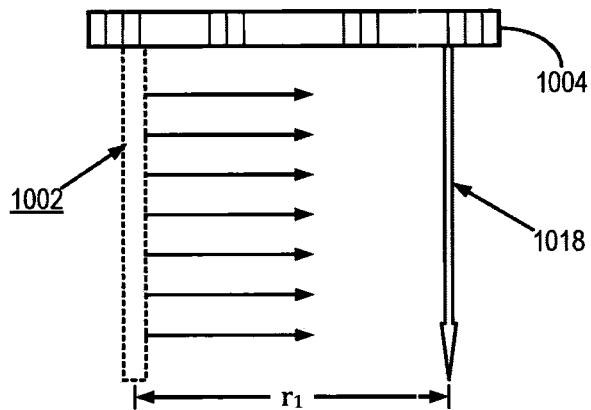
FIGS. 10A-10C are pictorial representations of examples of methods for measuring shear wave propagation using focused ultrasound detection beams.
Figure 10B:
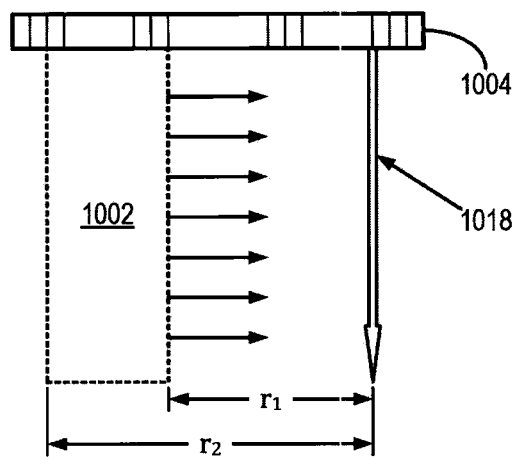
Figure 10C:
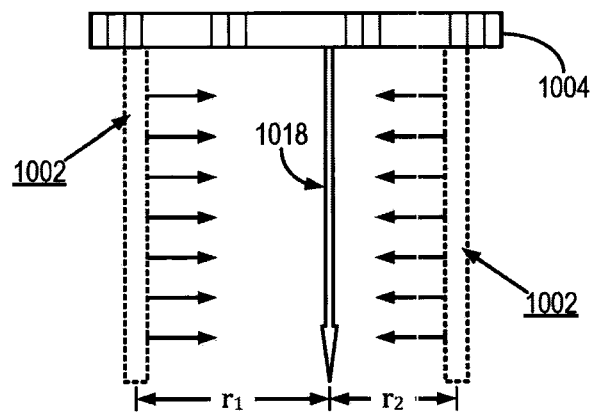

The detection and measurement of shear waves can be achieved with both traditional focused ultrasound, or by plane wave flash imaging. Flash imaging generates a two-dimensional image with a single unfocused ultrasound transmission and, therefore, can be used to produce a time series of images of shear wave propagation in two dimensions. If properly processed, this time series of images can generate a two-dimensional elasticity image from just one ultrasound push. Focused ultrasound beams are limited to tracking motion along the ultrasound ray 1018; therefore, such shear wave detection is not as flexible. However, an average shear wave speed can still be estimated along the ultrasound beam axis using the arrival time of shear waves propagating through the distances $r_1$, $r_2$, or $(r_1-r_2)$, as illustrated in FIGS. 10A-10C.

Direct inversion can be used to estimate tissue elasticity and viscosity if tissue motion due to shear waves can be measured across space and time with high signal-to-noise ratio ("SNR"). Direct inversion requires the calculation of second order derivatives of tissue motion in both spatial and time domains, which makes this approach sensitive to noise in the tissue motion data. Shear waves generated by ultrasound push beams are generally weak and low in SNR. A single focused (FIG. 1) or unfocused beam (FIG. 2A, 2B) will produce transient shear waves propagating outwards from the center of the push beam. At any given time instance, tissue motion is present in small regions where the shear wave fronts arrive. This can lead to unreliable estimates by direct inversion at other regions where there is no significant tissue motion due to shear waves.

Through the foregoing description, it has been generally shown that consistent shear wave speeds can be obtained at different depths using unfocused push beams. Because only one sub-aperture of transducer elements is used for each push beam, multiple sub-apertures of elements at different spatial locations can be used to simultaneously transmit unfocused push beams. This configuration of transmission is referred to as a "comb-push." The comb-push technique may be used to develop a two-dimensional shear elasticity imaging method calledcomb-push ultrasound shear elastography ("CUSE"). In CUSE, shear waves produced by each push beam can be treated as an independent realization of a single unfocused push.

Shear waves from different unfocused push beams interfere with each other constructively and destructively and eventually fill the entire field-of-view ("FOV"). To achieve robust shear wave speed estimation, a directional filter is used to extract left-to-right ("LR") propagating shear waves and right-to-left ("RL") propagating shear waves from the interfering shear wave patterns. A time-of-flight based shear wave speed estimate method may be used to recover local shear wave speed at each pixel from both LR waves and RL waves. A final shear wave speed map may then be combined from the LR speed map and RL speed map. Because comb-push pulses produce shear wave motions with high amplitude at all image pixels, including at the push beam areas, both shear wave speed at the "source free" areas and shear wave speeds at the push beam areas can be recovered. Thus, CUSE enables a full FOV two-dimensional reconstruction of a shear elasticity map with only one data acquisition. Safety measurements demonstrate that all regulated parameters of the ultrasound output level used in a CUSE sequence are well below the FDA limits for diagnostic ultrasound.

Below, the principles of CUSE, including the realization of the comb-push sequence, shear wave motion detection, directional filter implementation, and post-processing for two-dimensional shear wave speed map reconstruction are described.

Figure 11A:
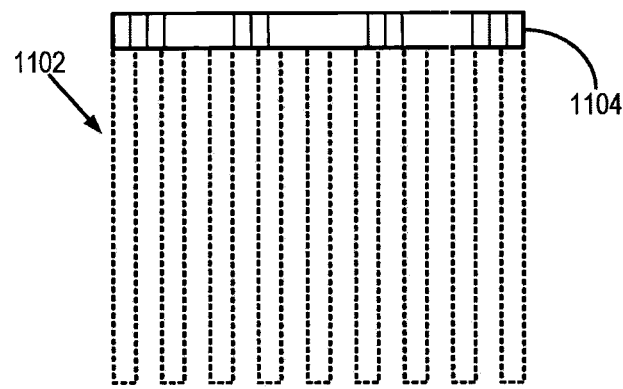
FIGS. 11A-11C are pictorial representations of examples of methods for using a plurality of unfocused ultrasound beams arranged in a comb pattern to produce shear waves in accordance with some embodiments of the present invention.
Figure 11B:
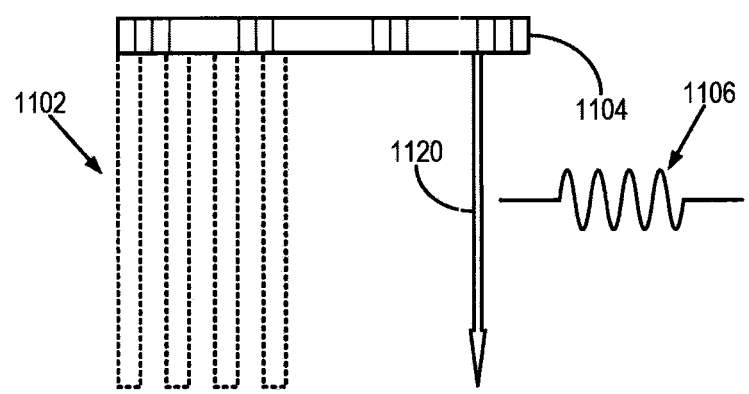
Figure 11C:
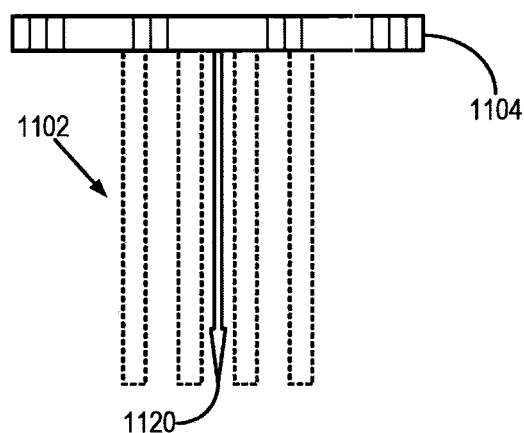

Referring now to FIGS. 11A-11C, multiple unfocused push beams that are spatially spaced apart, similar to a "comb" pattern, can be utilized for shear wave generation. Such a comb-push field 1102 will generate higher SNR shear wave motions throughout the entire region under the aperture of the transducer 1104. A single comb-push can also generate shear waves lasting for a long time at any given spatial location because shear waves from different push beams in the comb arrive at different times. The combined effect is that strong shear wave signals covering the entire spatial and time domain are produced, which can improve the SNR and, therefore, the reliability of direct inversion. Although the comb-push pulses illustrated in FIGS. 11A-11C are shown to be composed of evenly spaced pulses, it will be appreciated by those skilled in the art that the comb push pulse can also be composed of unevenly spaced push pulses.

By way of example, in a comb-push 1102, the elements of an array transducer 1104, such as a linear array transducer, used to produce push beams are divided into a number of subgroups, as shown in FIG. 11A. For example, the elements may be divided into nine subgroups and labeled from subgroup one to nine. Each subgroup of push beam looks like a tooth of a comb, thus this kind of push pulse is referred to as a "comb-push." As an example, when five subgroups are used to form a comb-push it may be called a "5-tooth comb-push."

After comb-push transmission, the ultrasound system is switched to an imaging mode, such as plane wave imaging mode, with all transducer elements used to detect the propagating shear waves. A plane wave imaging compounding method may be used to improve signal-to-noise-ratio ("SNR") of shear wave displacement tracking. As an example, three frames at three different steering angles may be compounded to obtain one imaging frame.

Each unfocused beam in the CUSE imaging technique generates two shear wave fronts propagating towards opposite directions. As mentioned above, one shear wave front may propagate left-to-right ("LR") and the other right-to-left ("RL"). Shear waves from different subgroups of the comb-push constructively and destructively interfere with each other, and a complicated shear wave field is created as a result. Although sufficient shear waves are produced in the medium with this method, the destructive interference decreases the amplitude of the shear wave motion measured for shear wave velocity estimates. To remove the destructive interference and separate LR and RL shear waves, a directional filter may be used. Examples of directional filters that are useful for this purpose are described, for example, by T. Deffieux, et al., in "On the Effects of Reflected Waves in Transient Shear Wave Elastography," *IEEE Trans Ultrason Ferroelectr Freq Control*, 2011; 58:2032-2305.

Referring particularly to FIG. 11B, a comb push with a motion detection ultrasound beam 1120 placed outside the comb. Shear waves from different push beams 1102 of the comb arrive at the detection beam 1120 position at different times because the propagation distance is different for each push beam 1102. Therefore, the detected shear wave signal 1106 will have multiple peaks along the time axis. Shear wave speed of the medium can be calculated from the time interval between these peaks, or by the frequency of the detected time signal, and the distance, r, between the push beams 1102 of the comb. The concept of using a spatially modulated push field, similar to a comb as described herein, for shear wave generation was proposed by McAleavey et al., in "Shear-Modulus Estimation by Application of Spatially-Modulated Impulsive Acoustic Radiation Force," *Ultrasonic Imaging*, 2007; 29(2):87-104. However, the approach taught by McAleavey used a Fraunhofer zone focused beam, which occurs at the intersection of two plane waves, or a single focused beam sequentially translated over several push positions to produce the spatially modulated push field. The unfocused beams proposed here are more flexible for generating push fields with different spatial modulation features. At the same time, the spatial modulation is expected to maintain over a very large depth range with the unfocused beams as compared to those produced with focused ultrasound.

McAleavey also taught placing the detection beam outside the spatially modulated field. Referring now to FIG. 11C, using the comb of unfocused ultrasound energy 1102 described above, a detection beam 1120 can be placed within the comb push field 1102. If all the push beams 1102 are placed symmetric about the detection beam 1120, shear waves 1106 from left side push beams 1102 will arrive at the detection beam 1120 at the same time as the shear waves 1106 from the push beams 1102 to the right side of the detection beam 1120. As a result, these shear waves 1106 add constructively and the shear wave magnitude is doubled. Shear wave amplitude is, thus, increased, leading to higher SNR for shear wave speed estimation.

Shear wave speed may be estimated using the time-of-flight algorithm by cross-correlating recorded particle velocity profiles along the lateral direction. By way of example, two points separated by eight ultrasound wavelengths (e.g., eight pixels) at the same depth are used to calculate local shear wave speed of the pixel in the middle of the FOV. The particle velocity profiles may be Tukey windowed so that both ends of the signal are forced to be zero, thereby facilitating more robust cross-correlation. The velocity profiles may also be interpolated before cross-correlation. As an example, the velocity profiles may be interpolated by a factor of five.

Figure 11D:
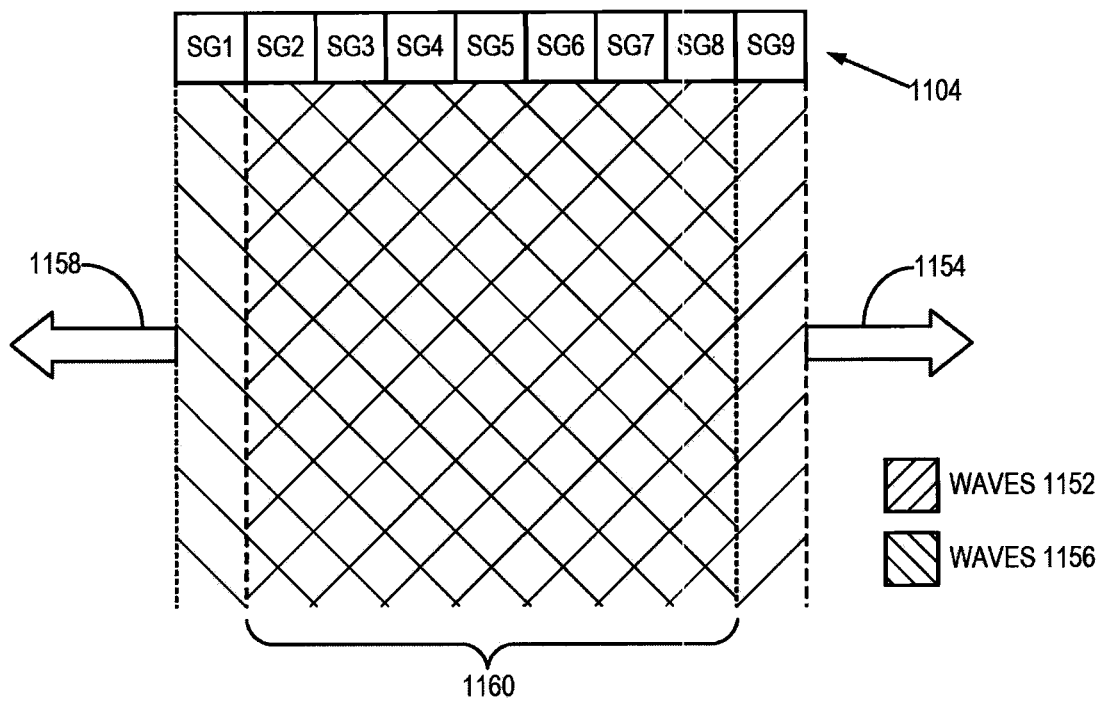
FIG. 11D is a pictorial representation of two groups of shear waves that propagate in different directions and that are produced using comb push pulses, such as those illustrated in FIGS. 11A-11C.

One advantage of CUSE imaging is that only one data acquisition is required to reconstruct a full FOV two-dimensional shear wave speed map. This advantage is described now with respect to the example configuration illustrated in FIG. 11D, where an ultrasound transducer 1104 is used to produce a first group of shear waves 1152 propagating in a first direction 1154 and a second group of shear waves 1156 propagating in a second direction 1158. By way of example, the first direction may be a left-to-right ("LR") direction and the second direction may be a right-to-left ("RL") direction. Continuing with this example for illustrative purposes, if a directional filter is used, the shear waves in the first group 1152 will propagate under subgroups SG2-SG9 and the shear waves in the second group 1156 will propagate under subgroups SG1-SG8. Thus, the shear wave speed at these areas can be recovered. However, the shear waves in the first group 1152 cannot cover the area under subgroup SG1 and the shear waves in the second group 1156 cannot cover the area under subgroup SG9. Therefore, a combination method is used to combine the shear wave speed map for the first group of shear waves 1152 and the shear wave speed map for the second group of shear waves 1156 so that a full FOV speed map can be obtained. The region under subgroup SG1 is reconstructed using only the second group of shear waves 1156 and region under subgroup SG9 is reconstructed using only the first group of shear waves 1152. The regions 1160 under subgroups SG2-SG8 are reconstructed by averaging the shear wave speed estimates from both the first group of waves 1152 and the second group of wave 1156.

Figure 14:
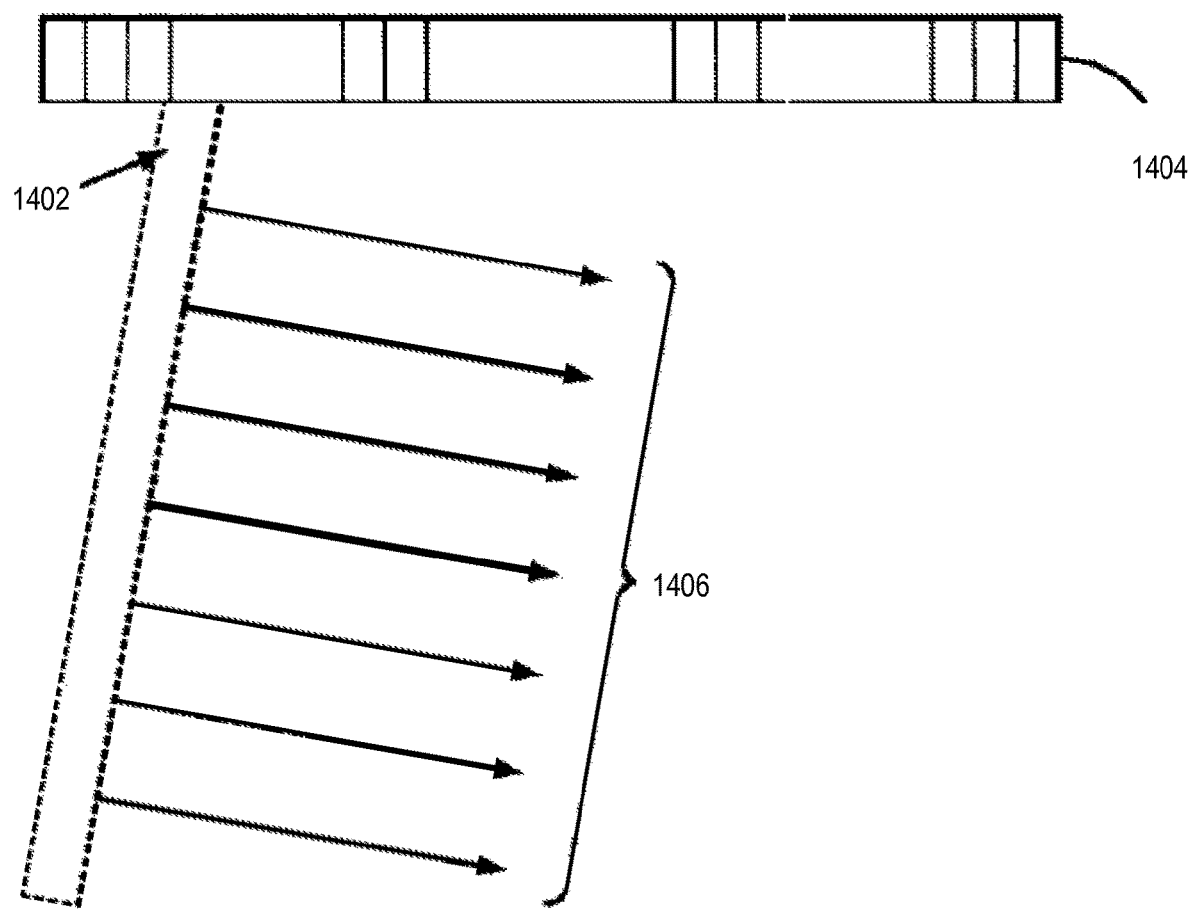
FIG. 14 is a pictorial representation of an example of an unfocused ultrasound beam generated off-center of an ultrasound transducer, with the unfocused ultrasound beam at a non-normal angle relative to the transducer, to produce shear waves propagating outward from a region of insonification produced in response to the unfocused ultrasound.

Although the foregoing description has been provided with respect to ultrasound push beams that are generated perpendicular, or substantially perpendicular, to the ultrasound transducer surface, it will be appreciated by those skilled in the art that the ultrasound push beams may also be steered such that they are not normal to the transducer surface. Referring to FIG. 14, the ultrasound energy 1404 is transmitted at an angle that is not normal to the transducer 1402, thereby generating shear waves 1406. In such instances, and when directional filtering is used to mitigate interference between shear waves travelling in different directions, such directional filtering may be modified to extract shear waves travelling at arbitrary angles. An example of using directional filters for arbitrary angles is described by A. Manduca, et al., "Spatio-Temporal Directional Filtering for Improved Inversion of MR Elastography Images," Medical Image Analysis, 2003; 7:465-473.

An advantage of using unfocused ultrasound energy to produce shear waves as described herein is that very few transducer elements need to be energized. Therefore, the transmit board does not need to produce a great deal of energy in order to produce a great deal of power on each of the transducer elements. The result of this is that the ultrasound push can be very long without overtaxing the transmit board because so few elements are used and because there is no need to have a large aperture to make a focus at some depth in the tissue. A focused ultrasound beam can easily exceed the FDA limits for diagnostic ultrasound and, therefore, a focused push tone burst cannot use the full voltage deliverable by the ultrasound system. In contrast, the intensity of the ultrasound energy is low for the method described herein because the beam is not focused. Thus, the mechanical index and intensity of the ultrasound beam should be well below the FDA limits. As a result, very high voltage can be used to produce the ultrasound push beams, which in turn can produce larger tissue motions. Another advantage of the herein described method is that because the mechanical index is low and because the intensity is low, the shear waves can be induced at a high pulse repetition rate, thereby allowing for many measurements in time, which is advantageous for dynamic measurements, such as through the cycle of the heart.

One potential challenge for this method is that tissue motion generated by a unfocused beam may be low compared to that generated by a focused beam. Therefore the SNR for shear wave detection may not be as high. There are a number of ways to increase tissue motions. As indicated above, higher transmit voltages can be used to obtain larger tissue motions because it is unlikely that an unfocused ultrasound beam will exceed FDA limits on intensity. In addition, a much longer tone burst can be transmitted to produce larger tissue motion because a unfocused beam uses fewer transmit elements and less energy; thus, power droop of the transmit board is less of an issue. Finally, a running average along the depth of the ultrasound beam can be used to improve the SNR of shear wave detection because shear wave propagation is relatively uniform along the depth direction. To obtain motion deep in the tissue, ultrasound with lower frequency can be used to achieve better penetration.

Figure 12:
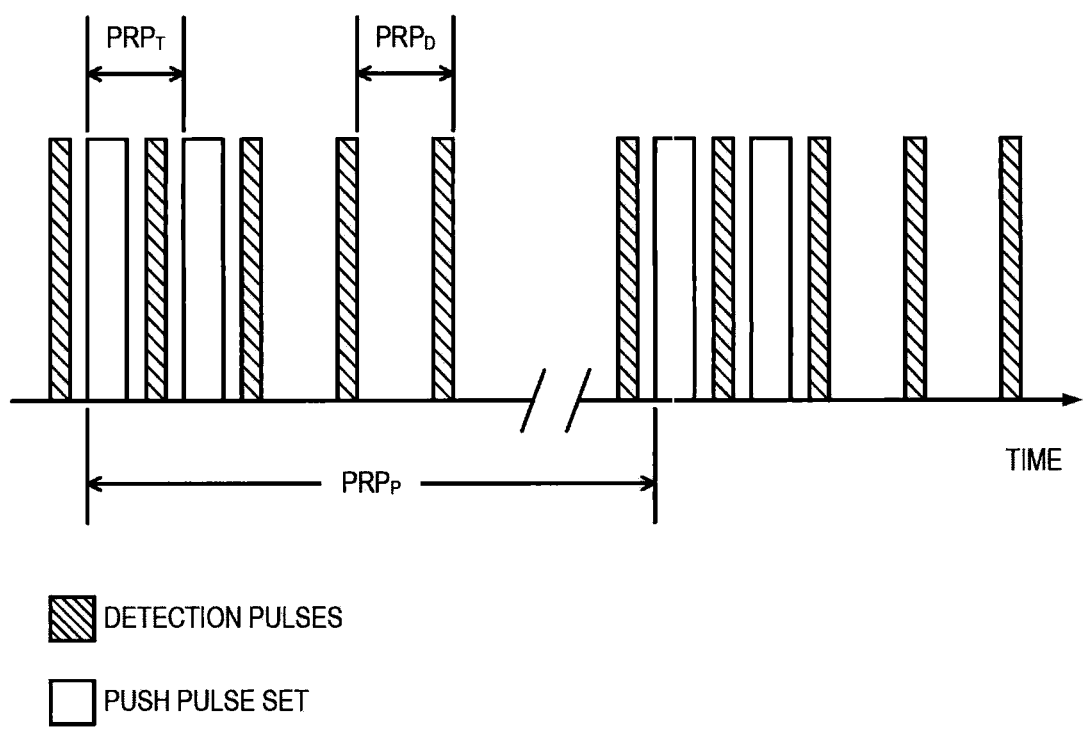
FIG. 12 is a pictorial representation of a series of short ultrasound tone bursts interlaced with motion detection pulses that effectively represent a long push tone burst.

If tissue motion must be measured during a long tone burst, the long tone burst can be replaced with multiple short tone bursts that are interlaced with motion detection pulses. Referring now to FIG. 12, the short tone bursts effectively represent a long push tone burst to tissues because the tissue response is relatively slow; therefore, the tissue does not recover from the each short tone burst before the next short tone bursts is applied. Detection pulses can, therefore, be added between these short tone bursts to measure tissue motion during the long push duration. Examples of methods of this nature are described, for example, in U.S. Provisional Patent Application No. 61/327,539, which is herein incorporated by reference in its entirety. The difference between the previously described method and the one described herein is that the short tone bursts used in the present method utilize unfocused ultrasound. Limited diffraction beams can also be used to generate unfocused beams that extend over a large axial depth range. Limited diffraction beams use all transducer elements to produce the unfocused beam and, therefore, can generate more tissue motion as a result of the more ultrasound energy present in the unfocused beam. Previous methods for using limited diffraction beams require the use of an annular transducer array, or a two-dimensional transducer. With the present method, however, a one-dimensional, 1.5-dimensional, 1.75-dimensional, or two-dimensional transducer can be used to produce the unfocused push.

Figure 13:
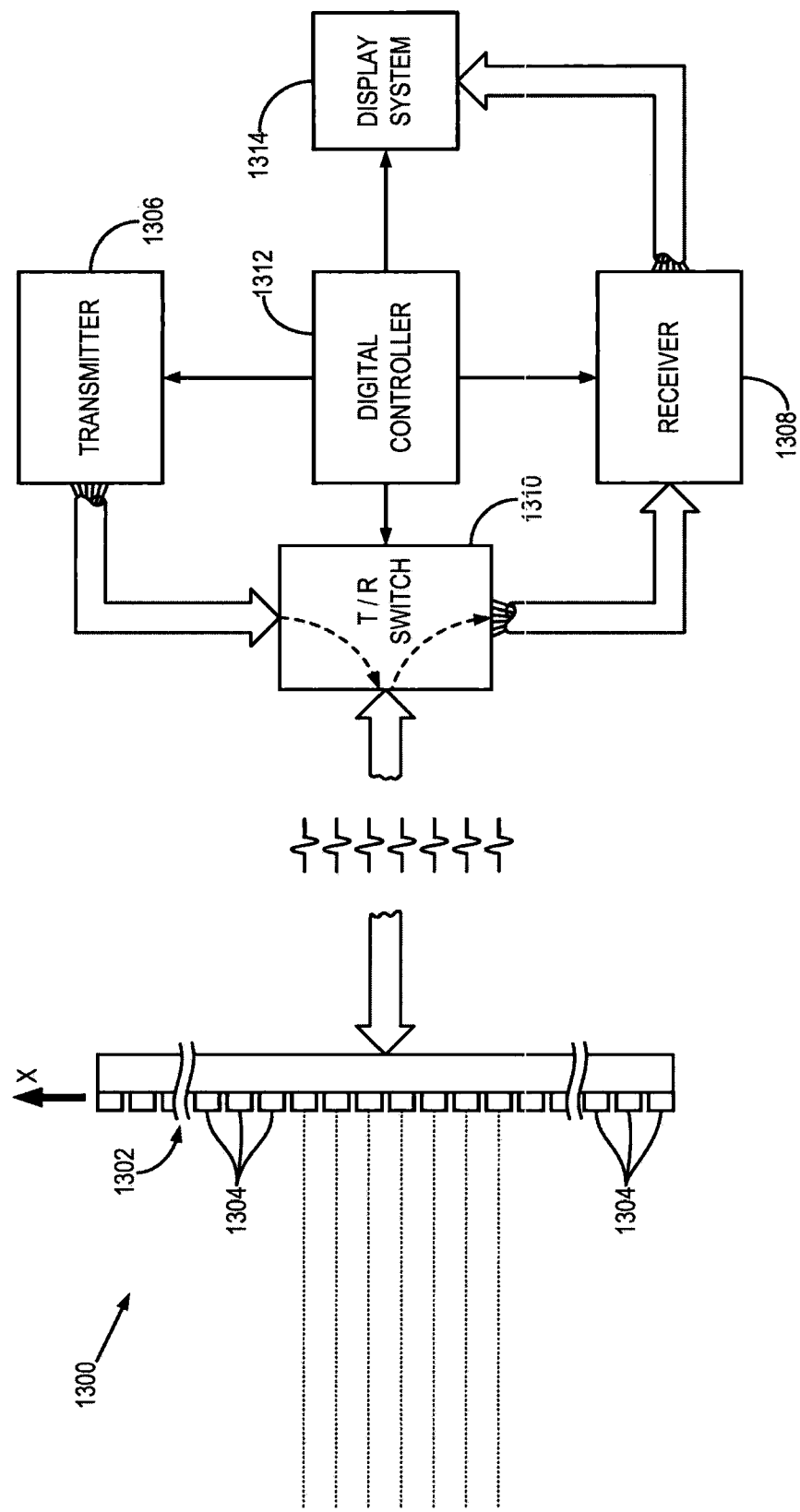
FIG. 13 is a block diagram of an example of an ultrasound system for use with some embodiments of the present invention.

Referring particularly to FIG. 13, an ultrasonic imaging system 1300 includes a transducer array 1302 that includes a plurality of separately driven transducer elements 1304. When energized by a transmitter 1306, each transducer element 1302 produces a burst of ultrasonic energy. The ultrasonic energy reflected back to the transducer array 1302 from the object or subject under study is converted to an electrical signal by each transducer element 1304 and applied separately to a receiver 1308 through a set of switches 1310. The transmitter 1306, receiver 1308, and switches 1310 are operated under the control of a digital controller 1312 responsive to the commands input by a human operator. A complete scan is performed by acquiring a series of echo signals in which the switches 1310 are set to their transmit position, thereby directing the transmitter 1306 to be turned on momentarily to energize each transducer element 1304. The switches 1310 are then set to their receive position and the subsequent echo signals produced by each transducer element 1304 are measured and applied to the receiver 1308. The separate echo signals from each transducer element 1304 are combined in the receiver 1308 to produce a single echo signal that is employed to produce a line in an image, for example, on a display system 1314. The transmitter 1306 drives the transducer array 1302 such that an ultrasonic beam is produced, and which is directed substantially perpendicular to the front surface of the transducer array 1302.

Although the present invention has been described with respect to the detection of shear waves with unfocused ultrasound, it will be appreciated by those skilled in the art that the present invention may also be applicable for detecting other tissue deformations resulting from an unfocused ultrasound push beam. Moreover, in addition to using ultrasound to detect tissue deformations produced by the application of unfocused ultrasound waves, other imaging modalities may be used for detection. For example, the tissue deformation may be detected using optical detection, magnetic resonance imaging, microwave detection, and other electromagnetic detection techniques.

The present invention has been described in terms of one or more preferred embodiments, and it should be appreciated that many equivalents, alternatives, variations, and modifications, aside from those expressly stated, are possible and within the scope of the invention. For example, another approach to imaging would be to transmit plane waves at multiple angles and to perform a sort of tomography or angle compound imaging.

The invention claimed is:

1. A method for controlling an ultrasound system to acquire measurement data suitable for measuring a mechanical property of a subject, the method comprising:
   a) controlling the ultrasound system via a controller to generate unfocused ultrasound energy with an ultrasound transducer of the ultrasound system and to transmit the unfocused ultrasound energy to a field-of-view (FOV) contained within the subject, thereby producing shear waves that propagate in the FOV in the subject;
   b) acquiring measurement data by using the ultrasound system to measure at least one location in the FOV in the subject in which the shear waves produced in step a) are present, the measurement data being suitable for calculating a mechanical property of the subject, wherein the measurement data are acquired by controlling the ultrasound system via the controller to generate ultrasound energy with the ultrasound transducer, thereby applying the ultrasound energy to the at least one location in the FOV in the subject using the ultrasound system;
   wherein the unfocused ultrasound energy applied to the subject in step a) includes a plurality of unfocused ultrasound beams extending outward from the ultrasound transducer in a comb-shaped pattern; and
   wherein the plurality of unfocused ultrasound beams are simultaneously generated, such that a combined effect of simultaneously generating the plurality of unfocused ultrasound beams in the comb-shaped pattern generates a first group of shear waves propagating in a first direction and a second group of shear waves propagating in a second direction such that the first group of shear waves
   and the second group of shear waves constructively interfere with each other within the FOV, thereby increasing a signal-to-noise ratio (SNR) of the measurement data, and destructively interfere with each other, thereby decreasing an amplitude of measured shear wave motion; and
   wherein step b) includes:
      forming a first subset of measurement data from the measurement data acquired in step b) by applying a first directional filter to the measurement data in order to extract measurements of the first group of shear waves propagating in the first direction and reduce destructive interference with the second group of shear waves, wherein the first subset of measurement data do not cover the entire FOV;
      forming a second subset of measurement data from the measurement data acquired in step b) by applying a second directional filter to the measurement data in order to extract measurements of the second group of shear waves propagating in the second direction and reduce destructive interference with the first group of shear waves, wherein the second subset of measurement data do not cover the entire FOV; and
      selectively combining the first subset of measurement data and the second subset of measurement data, generating output as combined measurement data that cover the entire FOV and have increased amplitude of measured shear wave motion by the reduced destructive interference between the first and second groups of shear waves.

2. The method as recited in claim 1 in which the ultrasound energy applied in step b) is at least one of focused ultrasound energy and unfocused ultrasound energy.

3. The method as recited in claim 1 in which the plurality of unfocused ultrasound beams are spaced apart evenly across a surface of the ultrasound transducer.

4. The method as recited in claim 1 in which the first direction and the second direction are opposite.

5. The method as recited in claim 1 in which the unfocused ultrasound energy applied in step a) is generated by an ultrasound transducer at an angle that is not normal to a surface of the ultrasound transducer.

6. A system for measuring a mechanical property of a subject, the system comprising:
   an ultrasound transducer;
   a controller in communication with the ultrasound transducer and configured to:
      a) control the ultrasound transducer to generate unfocused ultrasound energy and apply that unfocused ultrasound energy to a field-of-view (FOV) within the subject in order to produce shear waves that propagate in the FOV in the subject, wherein the unfocused ultrasound energy includes a plurality of unfocused ultrasound beams extending outward from the ultrasound transducer in a comb-shaped pattern, wherein the plurality of unfocused ultrasound beams are simultaneously generated, such that a combined effect of simultaneously generating the plurality of unfocused ultrasound beams in the comb-shaped pattern generates a first group of shear waves propagating in a first direction and a second group of shear waves propagating in a second direction such that the first group of shear waves and the second group of shear waves constructively interfere with each other within the FOV and destructively interfere with each other, thereby decreasing an amplitude of measured shear wave motion;
      b) control the ultrasound transducer to generate a second ultrasound energy and apply that second ultrasound energy to the FOV in the subject in order to acquire measurement data to measure at least one location in the FOV in the subject in which the shear waves produced by the transmitter are present;
      c) form a first subset of measurement data from the measurement data by applying a first directional filter to the measurement data in order to extract measurements of the first group of shear waves propagating in the first direction and reduce destructive interference with the second group of shear waves, wherein the first subset of measurement data do not cover the entire FOV;
      d) form a second subset of measurement data from the measurement data by applying a second directional filter to the measurement data in order to extract measurements of the second group of shear waves propagating in the second direction and reduce destructive interference with the first group of shear waves, wherein the second subset of measurement data do not cover the entire FOV; and
      e) selectively combine the first subset of measurement data and the second subset of measurement data, generating output as combined measurement data, the combined measurement data being suitable for calculating a mechanical property of the subject and having an increased signal-to-noise ratio caused by the shear waves propagating in different directions within the FOV constructively interfering with each other and increased amplitude of measured shear wave motion by way of the reduced destructive interference between the first and second groups of shear waves and destructive interference being reduced by the first and second directional filters.

7. The system as recited in claim 6 in which the second ultrasound energy applied is at least one of focused ultrasound energy and unfocused ultrasound energy.

8. The system as recited in claim 6 in which the controller is configured to control the ultrasound transducer to, in use, produce the plurality of unfocused ultrasound beams spaced apart evenly across a surface of the ultrasound transducer.

9. The system as recited in claim 6 in which the first direction and the second direction are opposite.

10. The system as recited in claim 6 in which the controller is configured to control the ultrasound transducer to apply the unfocused ultrasound energy at an angle that is not normal to a surface of the ultrasound transducer.

* * * * *